US00PP27247P3

(12) United States Plant Patent
Olesen

(10) Patent No.: US PP27,247 P3
(45) Date of Patent: Oct. 11, 2016

(54) HYBRID TEA ROSE PLANT NAMED 'POULHT009'

(50) Latin Name: ***Rosa* hybrid**
Varietal Denomination: Poulht009

(71) Applicant: Mogens Nyegaard Olesen, Fredensborg (DK)

(72) Inventor: Mogens Nyegaard Olesen, Fredensborg (DK)

(73) Assignee: Poulsen Rose A/S, Fredensborg (DK)

( * ) Notice: Subject to any disclaimer, the term of this patent is extended or adjusted under 35 U.S.C. 154(b) by 39 days.

(21) Appl. No.: 14/121,283

(22) Filed: Aug. 15, 2014

(65) Prior Publication Data

US 2016/0050812 P1 Feb. 18, 2016

(51) Int. Cl.
*A01H 5/02* (2006.01)

(52) U.S. Cl.
USPC ..... Plt./133

(58) Field of Classification Search
USPC ..... Plt./101, 130, 133
See application file for complete search history.

(56) References Cited

PUBLICATIONS

UPOV—International Union for the Protection of New Varieties of Plants—PLUTO: Plant Variety Database Feb. 19, 2016; citation for 'Poulht009' (1 pg total).*
Poulson Roser A/S "Perfection by Poulson" Hybrid Tea Poulsen—Main Varieties 2013 (2 pgs total).*
Retrieved from the Internet on Feb. 17, 2016 for www.poulsenroser.com/assortment/rosecollections/paramount/clausdalby.aspx (1 pg total).*

* cited by examiner

*Primary Examiner* — Susan McCormick Ewoldt

(57) ABSTRACT

A new garden rose plant of the Hybrid Tea class which has abundant, white flowers and attractive foliage. This new and distinct variety has shown to be uniform and stable in the resulting generations from asexual propagation.

3 Drawing Sheets

Botanical designation: *Rosa* hybrid.
Variety denomination: 'Poulht009'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulht009', originated as a single seedling from the stated cross.

The new variety may be distinguished from its male pollen parent and female seed parent primarily by the following characteristics. The female seed parent has light pink flowers, while the new plant has white flowers. The male pollen parent has an overall growth height of 150 to 200 cm, while the new variety is about 100 cm in height.

The objective of the hybridization of this rose variety was to create a new and distinct variety for garden use with unique qualities, such as:

1. Uniform and abundant white flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulht009' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulht009' was selected in the spring of 2007 by the inventor as a single plant from the progeny of the aforementioned hybridization.

Asexual reproduction of 'Poulht009' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulht009' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulht009'.

Specifically illustrated in FIG. 1 are open flowers.

Figure 1:
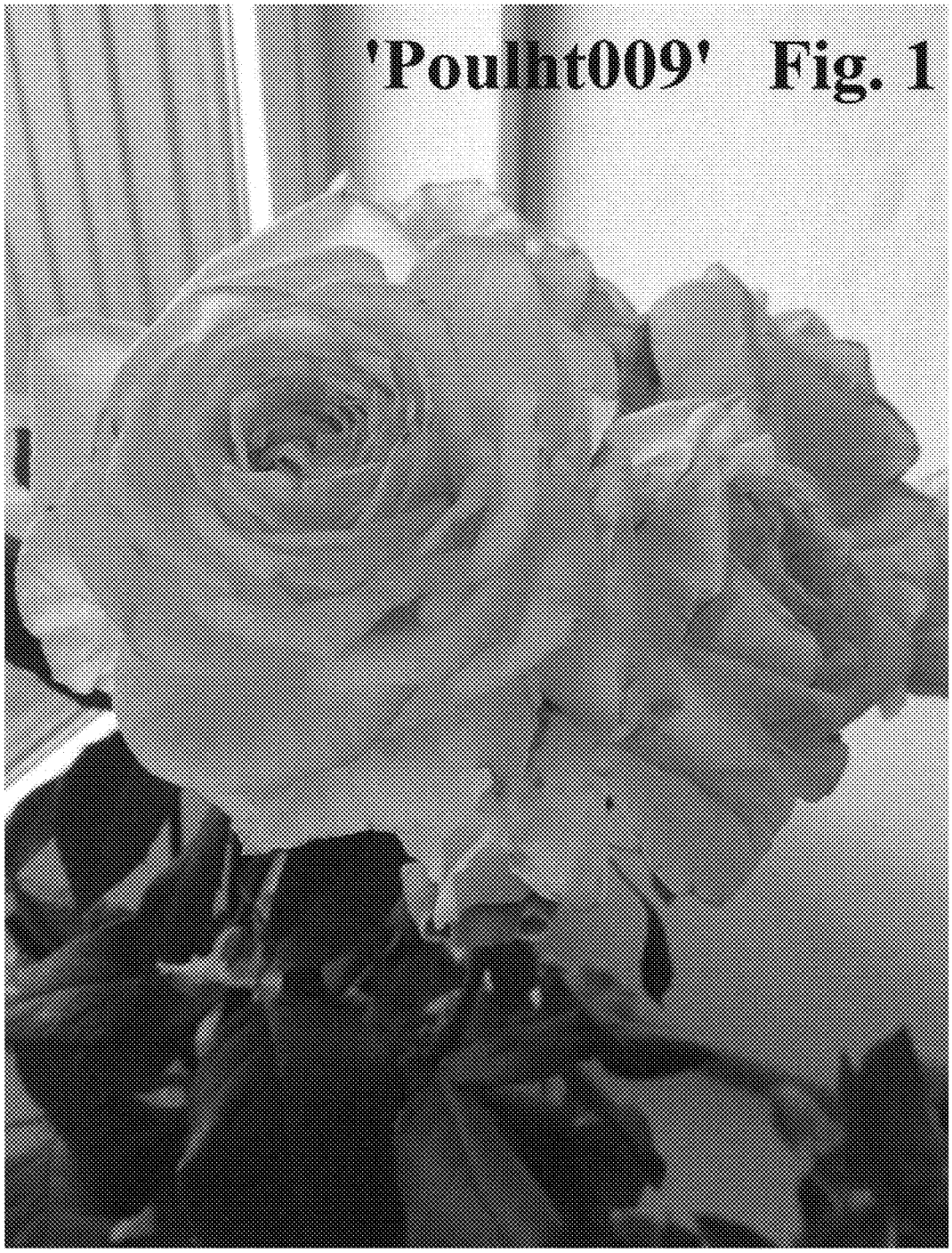
Figure 2:
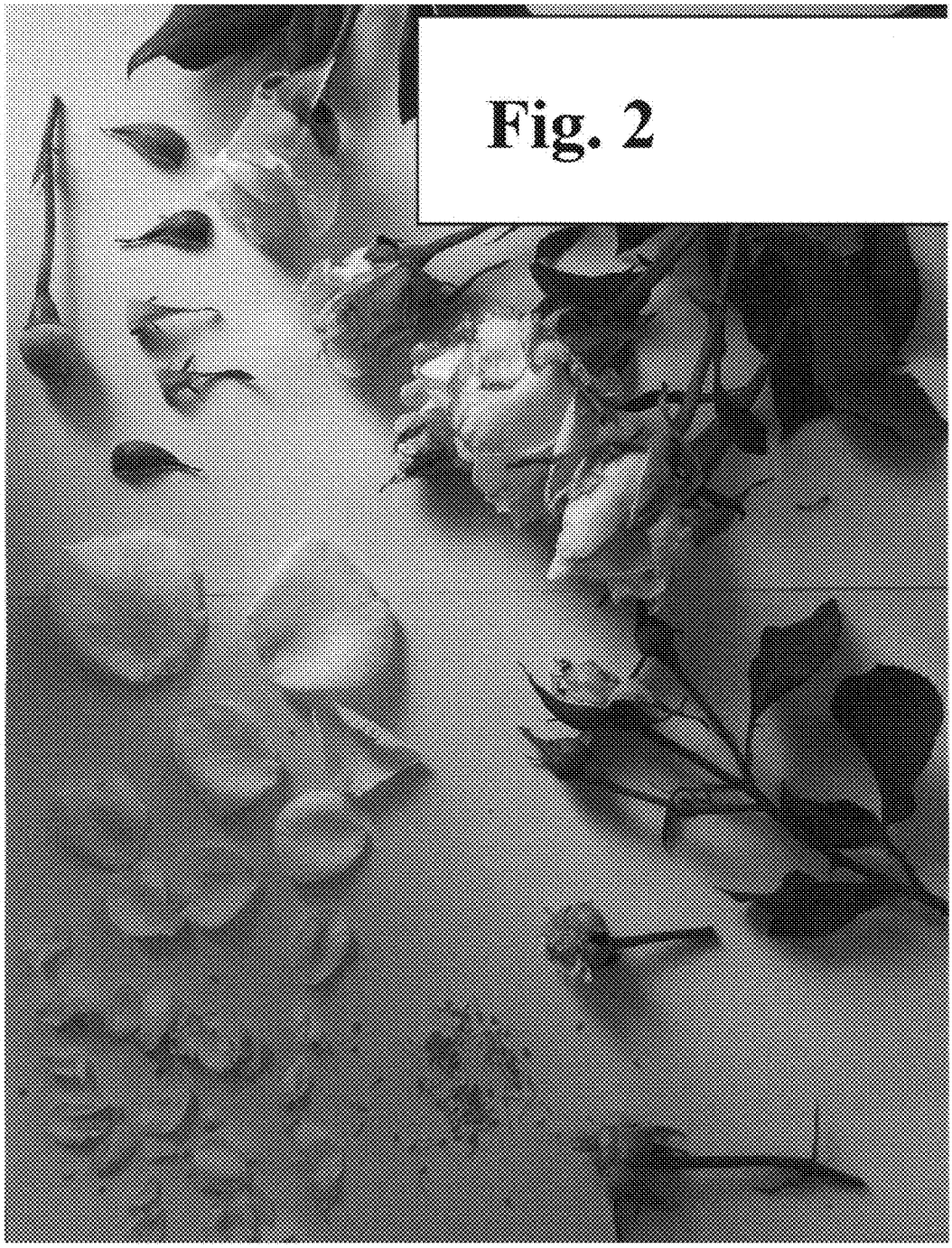
FIG. 2 shows open flowers on the branch, flower petals detached, reproductive flower parts and sepals detached.
Figure 3:
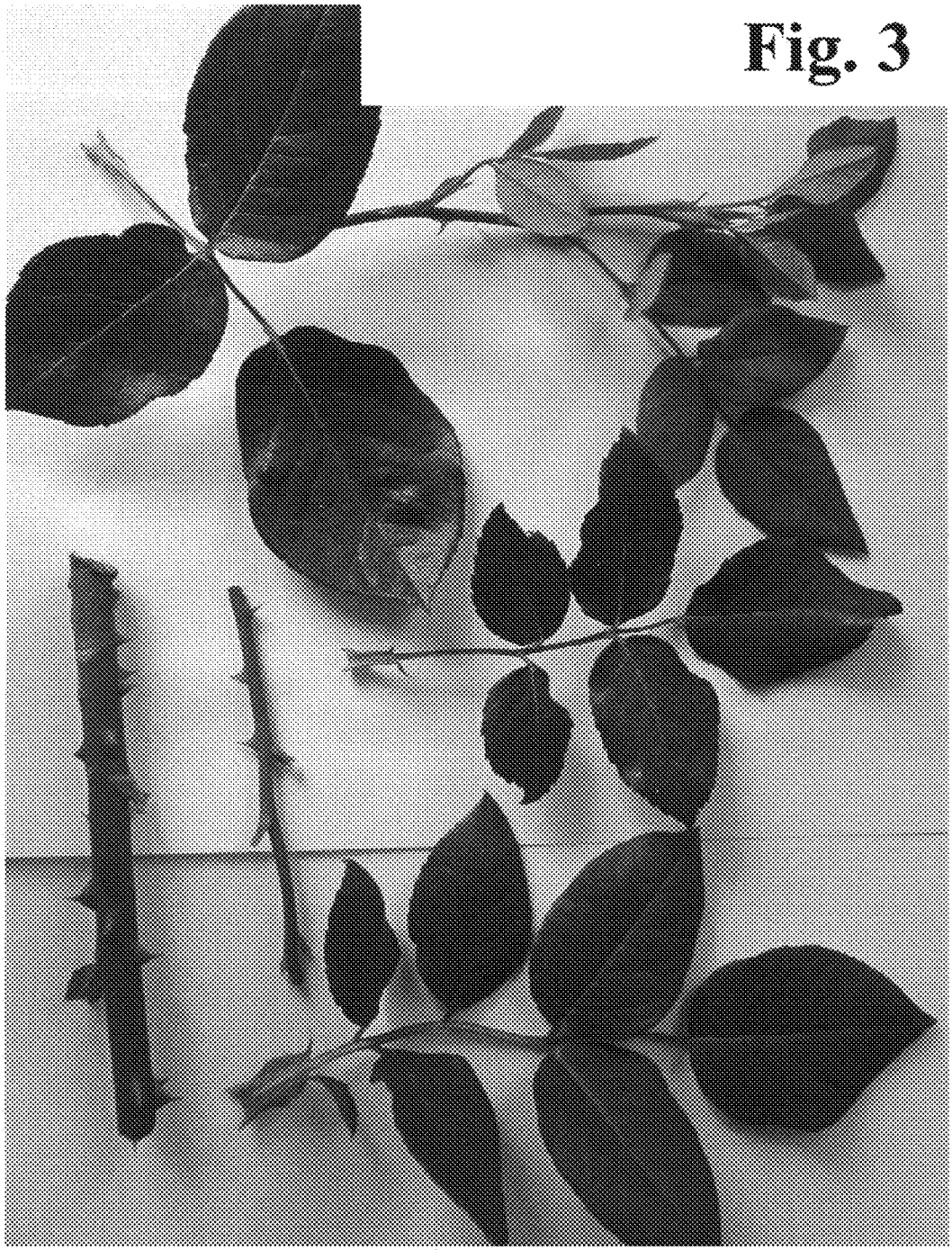
FIG. 3 shows mature and juvenile leaves and stems.

Plants shown are 2 years of age.

DETAILED DESCRIPTION OF THE VARIETY

The following is a description of 'Poulht009', as observed in its growth in in a field nursery in Marion County, Oreg.

Observed plants are 2 years of age, and were grown on their own roots. Color references are made using The Royal Horticultural Society (London, England) Colour Chart, 2001, except where common terms of color are used.

For a comparison, several physical characteristics of the rose variety 'JACsegra', U.S. Plant Pat. No. 19,017 are compared to 'Poulht009' in Chart 1.

CHART 1

| | 'Poulht009' | 'JACsegra' |
|---|---|---|
| Petal Count | 75 petals | 40 to 50 petals |
| Flower Diameter | 8 to 10 cm | 14 to 15 cm |
| General Tonality of Flower Color | White Group 155A | White Group 157D |

FLOWER AND FLOWER BUD

Blooming habit: Continuous.

Flower bud:

*Size.*—Upon opening, 35 mm in length from base of receptacle to end of bud. Bud diameter is 15 mm.

*Bud form.*—Ovoid.

*Bud color.*—As sepals divide petals are Green Yellow 1C.

*Sepal inner surface.*—Color: Green Group 138C. Surface: Smooth.

*Sepal outer surface.*—Color: Yellow-Green Group 144A with intonations of Greyed-Purple Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—30 mm long, 10 mm wide.

*Receptacle.*—Texture: Smooth. Size: 10 mm in height, 9 mm wide. Color: Yellow-Green Group 144A. Shape: Funnel.

*Pedicel.*—Surface: Smooth. Length: 25 to 50 mm. Diameter: 2 to 4 mm on average. Color: Yellow-Green Group 144B. Strength: Strong.

*Peduncle.*—Length: 1.5 to 20 cm. Diameter: About 5 mm. Color: Yellow-Green Group 146A with some intonations of Greyed-Red Group 178C. Texture: Smooth.

Flower bud development: Flower buds are borne in clusters of 5 to 7 flower buds per stem. Corymb development.

Flower bloom:

*Fragrance.*—Strong perfume.

*Duration.*—The blooms have a duration on the plant of approximately 7 to 10 days. Petals fall cleanly away from plant after flowers have fully matured.

*Size.*—Flower diameter is 80 to 100 mm when open. Flower depth is 40 mm.

*Flower shape.*—High centered very double, with a high pointed center which is tightly closed.

*Shape of flower, side view.*—The upper portion is a flattened convex. The lower portion is a flattened convex.

Petalage: Under normal conditions, flowers have 75 petals total, 25 of which are petaloids.

General tonality of flower: Open flowers are White Group 155A.

Petal color:

*Upon opening, outer petals.*—Upper surface: White Group 155A. Lower surface: White Group 155A.

*Upon opening, inner petals.*—Upper surface: White Group 155A. Lower surface: White Group 155A.

*Basal petal spots, upon opening.*—Upper surface: Green-Yellow Group 1C. Lower surface: Green-Yellow Group 1C.

*After opening, outer petals.*—Upper surface: White Group 155A. Lower surface: White Group 155A.

*After opening, inner petals.*—Upper surface: White Group 155A. Lower surface: White Group 155A.

*Basal petal spots, after opening.*—Upper surface: Green-Yellow Group 1A. Lower surface: Green-Yellow Group 1C.

Petals:

*Petal reflex.*—Strong on outer petals.

*Margin.*—Entire and uniform. Weak undulations.

*Shape.*—Generally broad elliptic. Apex shape: Rounded. Base shape: Rounded.

*Size.*—40 mm (l)×40 mm (w).

*Texture.*—Smooth.

*Thickness.*—Average.

Petaloids:

*Size.*—20 mm (l) by 15 mm (w).

*Shape.*—Apex and base are acute.

*Color.*—White Group 155A.

Reproductive flower parts:

*Pollen.*—None observed.

*Anthers.*—Size: 2 mm in length. Color: Orange Group 25B. Quantity: 50 on average.

*Filaments.*—Color: Green Yellow 1A. Length: 7 mm.

*Pistils.*—Length: 6 mm. Quantity: 45 on average.

*Stigmas.*—Color: Yellow Group 13B.

*Styles.*—Color: Orange-Red Group 33A.

*Location of stigmas.*—Inferior in location relative to the length of the filaments and the height of the anthers.

*Hips.*—None Observed.

PLANT

Plant growth: Upright, bushy. Plants are 100 cm in height, and 80 cm wide.

Stems:

*Color.*—Juvenile growth: Yellow-Green Group 146A. Mature growth: Yellow-Green Group 147B.

*Length.*—On average, canes are 75 cm from the base of the plant to the flowering portion.

*Diameter.*—10 mm.

*Internodes.*—On mature canes about 35 to 50 mm between nodes.

*Surface texture.*—Young wood: Smooth. Older wood: Small prickles.

Long prickles:

*Incidence.*—10 to 15 prickles per 10 cm of stem.

*Size.*—Average length of prickles on mature stems is 8 mm.

*Shape.*—Upper portion is deep concave. Lower portion is deep concave.

*Color.*—Juvenile prickles: Yellow-Green Group 146B. Mature prickles: Greyed-Red Group 182B.

Plant foliage:

*Compound leaf.*—150 to 200 mm (l)×100 to 150 (w).

*Quantity.*—3 leaves per 10 cm of stem on average.

*Leaf bearing angle to the stem.*—45 to 60 degrees.

*Color of juvenile foliage*.—Upper side: Yellow-Green Group 147B. Lower side: Yellow-Green Group 147C. Anthocyanin: Greyed-Red Group 181B.

*Color of mature foliage*.—Upper side: Yellow-Green Group 147A. Lower side: Yellow-Green Group 147C.

Plant leaves and leaflets:

*Stipules*.—Size: 20 mm long, 6 mm wide. Quantity: 2 per compound leaf. Shape: Linear, slightly broad based with outward extending apices. Margins: Finely serrated with many stipitate glands. Color: Yellow-Green Group 147A with intonations of Greyed-Red Group 181C.

Petiole:

*Length*.—About 35 mm.

*Diameter.*—2 mm.

*Upper surface.*—Color: Yellow-Green Group 147B.

*Lower surface.*—Color: Yellow-Green Group 147B.

Rachis:

*Length*.—About 25 mm.

*Upper surface.*—Color: Yellow-Green Group 147B.

*Lower surface.*—Color: Yellow-Green Group 147B.

Leaflet:

*Quantity*.—Normally 5 leaflets.

*Margins*.—Serrated.

*Size*.—On average terminal leaflets are 90 mm long, 50 mm wide.

*Shape*.—Generally elliptical. Base: Rounded. Apex: Mucronate.

*Texture*.—Rough.

*Thickness*.—Average.

*Arrangement*.—Odd pinnate.

*Venation*.—Reticulate.

*Glossiness*.—Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Hybrid Tea rose class named 'Poulht009', substantially as illustrated and described herein, due to its abundant white flowers, disease resistance, and extended period of bloom.

* * * * *

'Poulht009' Fig. 1